(12) United States Patent
Yasunaga (10) Patent No.: US 9,194,846 B2
(45) Date of Patent: Nov. 24, 2015

(54) NEEDLE ADAPTOR AND AUTOMATIC SAMPLER USING THE SAME

(75) Inventor: Kenichi Yasunaga, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 371 days.

(21) Appl. No.: 13/478,346

(22) Filed: May 23, 2012

(65) Prior Publication Data

US 2013/0014597 A1 Jan. 17, 2013

(30) Foreign Application Priority Data

Jul. 11, 2011 (JP) .................................. 2011-153235

(51) Int. Cl.
*G01N 30/24* (2006.01)
*G01N 30/18* (2006.01)

(52) U.S. Cl.
CPC .......... *G01N 30/24* (2013.01); *G01N 2030/185* (2013.01)

(58) Field of Classification Search
CPC ... G01N 30/24; G01N 30/20; G01N 35/1097; G01N 2010/8804; G01N 30/16; G01N 30/466; G01N 30/02; G01N 30/04
USPC .................... 73/863.01, 61.55, 864.21, 23.41, 73/864.91
See application file for complete search history.

(56) References Cited

U.S. PATENT DOCUMENTS

| | | | |
|---|---|---|---|
| 4,393,726 A * | 7/1983 | Tamm et al. | 73/864.84 |
| 4,476,017 A * | 10/1984 | Scharff et al. | 210/94 |
| 4,713,974 A | 12/1987 | Stone | |
| 5,188,730 A * | 2/1993 | Kronwald | 210/198.2 |
| 5,863,428 A * | 1/1999 | Ma et al. | 210/198.2 |
| 7,195,229 B2 | 3/2007 | Maeda | |
| 8,234,939 B2 | 8/2012 | Maeda et al. | |
| 8,266,973 B2 | 9/2012 | Maeda et al. | |
| 8,322,374 B2 | 12/2012 | Tomita | |
| 8,522,628 B2 | 9/2013 | Seki et al. | |
| 2003/0143123 A1* | 7/2003 | Maeda | 422/100 |

(Continued)

FOREIGN PATENT DOCUMENTS

| CN | 1192233 C | 3/2005 |
|---|---|---|
| CN | 101419204 A | 4/2009 |

(Continued)

OTHER PUBLICATIONS

Chinese Office Action dated Mar. 21, 2014, issued in corresponding Chinese Patent Application No. 201210175671.2 with partial English translation (11 pages).

*Primary Examiner* — Hezron E Williams
*Assistant Examiner* — Marrit Eyassu
(74) *Attorney, Agent, or Firm* — Westerman, Hattori, Daniels & Adrian, LLP (57) ABSTRACT

A needle adaptor mounted to one of a plurality of pipe connecting ports provided to a flow path switching valve to form an injection port into which a needle is inserted to inject a sample from a tip end of the needle is described. The needle adaptor comprises a dummy pipe having the same outer diameter as a normal pipe connected to the flow path switching valve, a port fixing portion for fixing the dummy pipe to the port, a needle seal for retaining the tip end of the needle to connect the needle and the dummy pipe and a needle seal housing mounted to the port fixing portion to retain the needle seal. The port fixing portion has the same shape as a port fixing portion of a pipe connecting member for connecting the normal pipe to the pipe connecting port.

13 Claims, 8 Drawing Sheets

(56) References Cited

U.S. PATENT DOCUMENTS

| | | | |
|---|---|---|---|
| 2004/0175833 A1* | 9/2004 | Tatsumi | 436/49 |
| 2007/0095158 A1* | 5/2007 | Maeda | 73/864 |
| 2009/0100942 A1* | 4/2009 | Maeda et al. | 73/863.01 |
| 2011/0247405 A1 | 10/2011 | Yasunaga et al. | |

FOREIGN PATENT DOCUMENTS

| | | |
|---|---|---|
| CN | 101680823 A | 3/2010 |
| CN | 101849126 A | 9/2010 |
| CN | 201859140 U | 6/2011 |
| JP | 56-97867 A | 8/1981 |
| JP | 57-16351 A | 1/1982 |
| JP | 3-35160 A | 2/1991 |
| JP | 2629539 B2 | 7/1997 |
| JP | 2003-215118 A | 7/2003 |
| JP | 2005-134217 A | 5/2005 |
| JP | 3129218 U | 2/2007 |
| JP | 2009-276355 A | 11/2009 |
| WO | 2010/044126 A1 | 4/2010 |
| WO | 2011/052445 A1 | 5/2011 |

* cited by examiner

NEEDLE ADAPTOR AND AUTOMATIC SAMPLER USING THE SAME

BACKGROUND OF THE INVENTION

1. Field of the Invention

The present invention relates to a needle adaptor into which a needle, containing a taken-in sample, is inserted to inject the sample and to an automatic sampler using the needle adaptor.

2. Description of the Related Art

An automatic sampler for injecting a sample into an analytical flow path of a liquid chromatograph includes a flow path switching valve having a plurality of ports and switching connection between the ports as well as a needle for taking in the sample. The flow path switching valve has the ports connected to the analytical flow path of the liquid chromatograph via pipes and the port forming an injection port into which the needle is inserted and connected. By connecting the ports and injecting the sample from the needle into the injection port, the flow path switching valve introduces the sample into the analytical flow path of the liquid chromatograph (see Japanese Unexamined Patent Publication No. 2003-215118). An example of a flow path configuration of such an automatic sampler is shown in FIG. 6.

Figure 6:
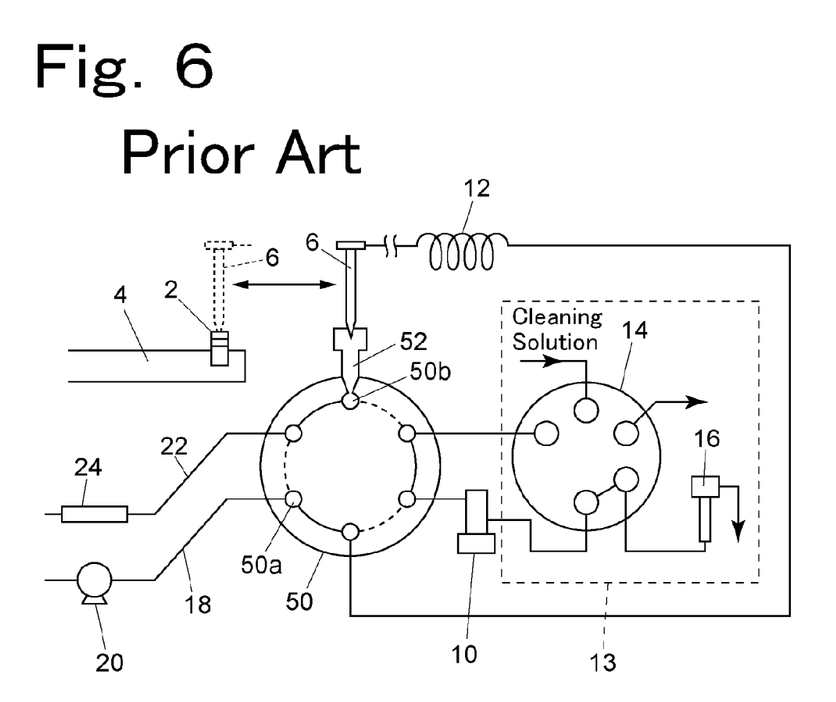
FIG. 6 is a flow path block diagram schematically showing an example of a conventional automatic sampler.

The automatic sampler in FIG. 6 includes a plurality of pipe connecting ports 50a, a port 50b for an injection port, and a flow path switching valve 50 for switching connection between the ports. A needle adaptor 52 is mounted to the port 50b for the injection port and the needle adaptor 52 forms the injection port for injecting the sample with a needle 6. The automatic sampler also includes the needle 6 and a syringe pump 10 connected, via pipes, to the pipe connecting ports 50a of the flow path switching valve 50. The needle 6 is connected to the syringe pump 10 by the flow path switching valve 50 to thereby suction and discharge a solvent from its tip end.

The needle 6 can be moved to a position of the needle adaptor 52, a position of a sample vial 2 on a rack 4 disposed in an apparatus, and a position of a cleaning port 16 of a cleaning mechanism 13. The needle 6 inserts its tip end into the sample vial 2 to suction the sample, keeps the sample in a sample loop 12, and then moves to the position of the needle adaptor 52 to inject the sample into the injection port.

An upstream analytical flow path 18 and a downstream analytical flow path 22 forming an analytical flow path of the liquid chromatograph are connected to the two pipe connecting ports 50a of the flow path switching valve 50. The upstream analytical flow path 18 includes a solvent delivery pump 20 for delivering a mobile phase and the downstream analytical flow path 22 includes an analytical column 24 and a detector (not shown). By inserting and connecting the needle 6 into the needle adaptor 52 and switching the state of the flow path switching valve 50 so that the upstream analytical flow path 18, the needle 6, and the downstream analytical flow path 22 are connected, the sample taken in from the tip end of the needle 6 can be introduced into the analytical column 24 by the mobile phase.

Figure 7A:
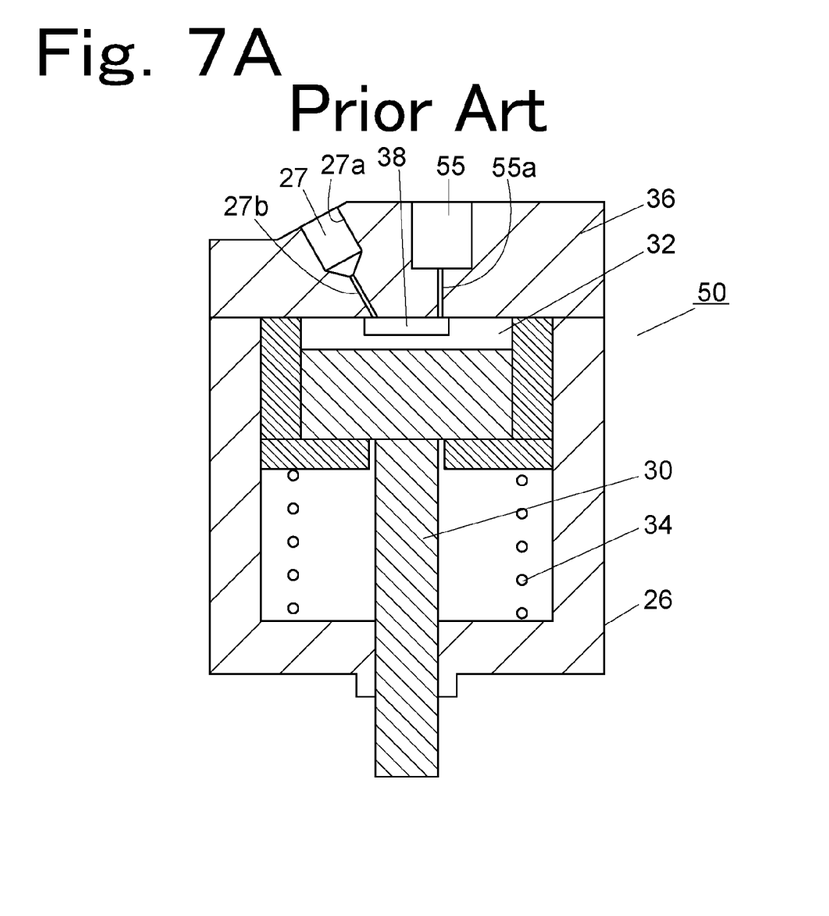
Figure 7B:
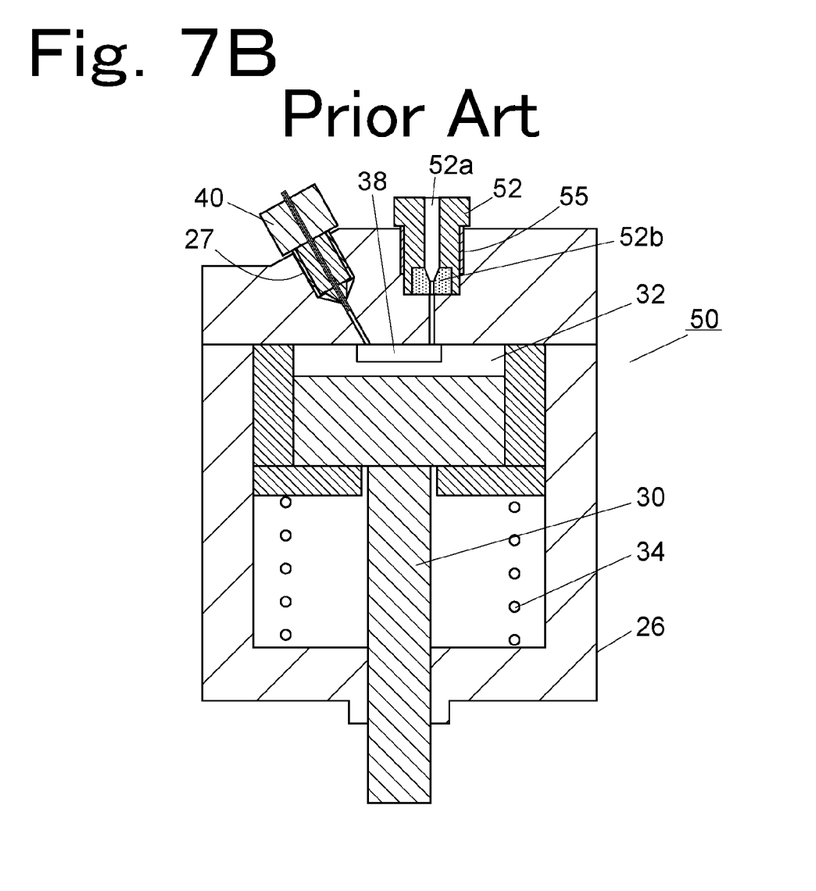

An example of a structure of the flow path switching valve 50 will be described with reference to sectional views in FIGS. 7A and 7B.

Each of the pipe connecting ports 27 includes a connecting hole 27a formed in an upper face of a stator 36 and a flow path 27b and the port for the injection port includes a connecting hole 55 formed in the upper face of the stator 36 and a flow path 55a. In a valve body 26, a circular columnar rotor 32 is housed with one of its circular faces oriented toward the upper face of the stator 36. One end of a shaft 30 is connected to the other circular face of the rotor 32, and the other end of the shaft 30 extends outside from a lower face side of the valve body 26 and is driven by a driving mechanism (not shown) disposed outside.

The one circular face of the rotor 32 and a lower face of the stator 36 are disposed to come in direct contact with each other. The rotor 32 is provided with a port connecting flow path 38 for connecting the adjacent ports in the upper face of the stator 36. When the shaft 30 rotates, the rotor 32 rotates as well to switch the flow paths. In order to increase liquid tightness between the rotor 32 and the stator 36, the rotor 32 is pushed against the stator 36 by a spring 34.

A bottom portion of each of the connecting holes 27 in the upper face of the stator 36 communicates with the lower face of the stator 36 through the flow path 27b and a bottom portion of the port hole 55 for the injection port communicates with the lower face of the stator 36 through the flow path 55a. A pipe fixing member 40 mounted to a tip end portion of the pipe can be fixed into the connecting hole 27 by engaging threads by screwing and the pipe can be connected to the flow path 27b by fixing the pipe fixing member 40. The needle adaptor 52 can be fixed into the port hole 55 for the injection port by engaging threads by screwing. The needle adaptor 52 has a hole 52a into which the needle 6 is to be inserted, and a needle seal 52b is disposed at a bottom portion of the hole 52a.

In the above example, in order to reduce a capacity of the flow path, through which the sample injected into the injection port from the needle passes, to suppress a phenomenon that a detection peak obtained by the liquid chromatograph is broad, the needle adaptor 52 is directly mounted into the port hole 55 for the injection port of the flow path switching valve 50. Because the pipe connecting member 40 and the needle adaptor 52 have different structures, it is necessary to provide the port 50b for the injection port separately from the pipe connecting port 50a. Therefore, the flow path switching valve 50 having the port 50b for the injection port cannot be formed by a general flow path switching valve, which increases the number of parts forming the automatic sampler.

SUMMARY OF THE INVENTION

It is an object of the present invention to form a flow path switching valve having an injection port by using a general flow path switching valve.

A needle adaptor according to the present invention is mounted to one of a plurality of pipe connecting ports provided to a flow path switching valve to form an injection port into which a needle is inserted to inject a sample from a tip end of the needle. The needle adaptor includes: a dummy pipe having the same outer diameter as a normal pipe connected to the flow path switching valve; a port fixing portion for fixing the dummy pipe to the port; a needle seal for retaining the tip end of the needle to connect the needle and the dummy pipe; and a needle seal housing mounted to the port fixing portion to retain the needle seal. The port fixing portion has the same shape as a fixing portion, which is fixed to the pipe connecting port to connect the pipe to the port, and connects the dummy pipe to the pipe connecting port.

In some embodiments of the needle adaptor according to the present invention, the port fixing portion and the needle seal housing may be integrally formed by using the same material. The dummy pipe, the port fixing portion, the needle seal, and the needle seal housing may be integrally formed by using an elastic material for forming the needle seal. In this way, it is possible to reduce the number of parts forming the needle adaptor and cost.

An automatic sampler according to the present invention includes: a syringe pump; a needle which can move in horizontal and vertical directions, moves to a position of a sample vessel containing a sample, inserts its tip end portion into the sample vessel, and suctions the sample by suctioning operation of the syringe pump; and a flow path switching valve which includes a plurality of pipe connecting ports in which the needle adaptor is mounted to one of the pipe connecting ports to form an injection port.

If the respective pipe connecting ports of the flow path switching valve are disposed uniformly in a circumferential direction in the same plane to be inclined a certain angle with respect to the plane, the flow path switching valve is preferably disposed to be inclined so that the injection port is in a vertical orientation. In this way, without complicating the driving of the needle, it is possible to insert and connect the needle into the injection port by driving the needle in the horizontal and vertical directions.

The port fixing portion of the needle adaptor according to some embodiments of the present invention and for fixing the dummy pipe to the port has the same shape as the fixing portion, which is fixed to the port of the pipe connecting member to connect the pipe to the port, and connects the dummy pipe to the pipe connecting port, and therefore, the needle adaptor can be fixed to the pipe connecting port similarly to the pipe connecting member. In this way, it is unnecessary to provide the port, which has a special structure for mounting the needle adaptor, to the flow path switching valve, and one of the ports of the general flow path connecting valve can be used as the injection port.

Because the automatic sampler according to the present invention includes the flow path switching valve, which has the plurality of pipe connecting ports, and in which the needle adaptor is mounted to one of the pipe connecting ports to form the injection port, the flow path switching valve having the special structure for the injection port is unnecessary, and one of the ports of the general flow path connecting valve can be used as the injection port. In this way, it is possible to reduce the number of parts forming the automatic sampler and cost.

BRIEF DESCRIPTION OF THE DRAWINGS

FIGS. 2A and 2B are sectional views showing a structure of a flow path switching valve including an injection port in the embodiment, wherein FIG. 2A shows a state in which a pipe connecting member and a needle adaptor are not fixed, and FIG. 2B shows a state in which the pipe connecting member and the needle adaptor are fixed;

FIGS. 3A and 3B are drawings showing the connecting members for connecting a pipe and a needle to ports of the flow path switching valve in the embodiment, wherein FIG. 3A is a sectional view of the connecting member for connecting the pipe and FIG. 3B is a sectional view of the needle adaptor;

FIGS. 7A and 7B are sectional views showing a structure of a flow path switching valve including an injection port in the conventional automatic sampler, wherein FIG. 7A shows a state in which a pipe connecting member and a needle adaptor are not fixed and FIG. 7B shows a state in which the pipe connecting member and the needle adaptor are fixed.

DETAILED DESCRIPTION OF THE INVENTION

Figure 1:
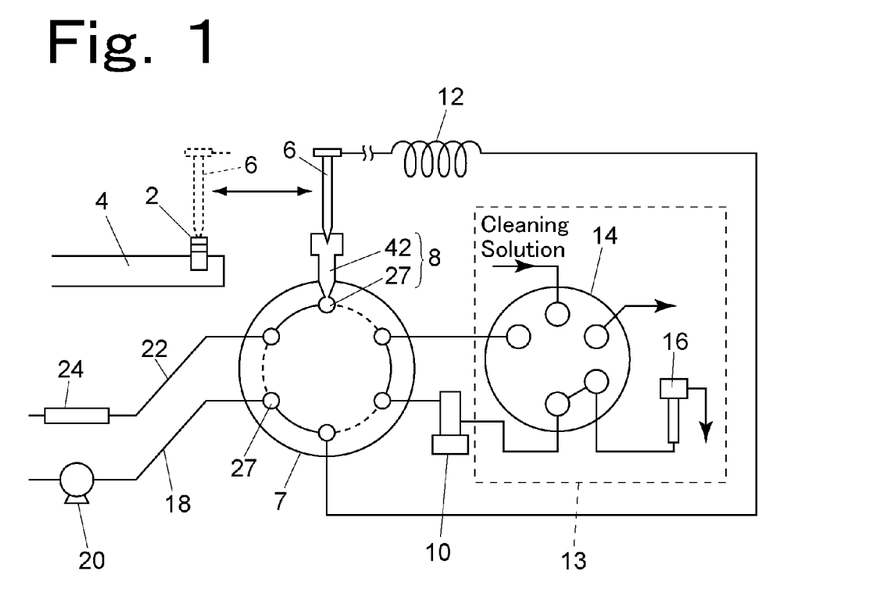
FIG. 1 is a flow path block diagram schematically showing an embodiment of an automatic sampler.

An embodiment of an automatic sampler for injecting a sample into an analytical flow path of a liquid chromatograph will be described with reference to FIG. 1.

A flow path switching valve 7 including six pipe connecting ports 27 is provided. A needle adaptor 42 is mounted to one of the pipe connecting ports 27 to form an injection port 8. To the other pipe connecting ports 27, a port of a flow path switching valve 14 forming a cleaning mechanism 13, a syringe pump 10, a base end of a needle 6, an upstream analytical flow path 18, and a downstream analytical flow path 22 are respectively connected by pipes.

By the flow path switching valve 7, a flow path connected to the base end of the needle 6 is connected to the upstream analytical flow path 18 or the syringe pump 10, and the injection port 8 is connected to the one port of the flow path switching valve 14 forming the cleaning mechanism 13 or the downstream analytical flow path 22. When the needle 6 and the upstream analytical flow path 18 are connected, the injection port 8 and the downstream analytical flow path 22 are connected. When the needle 6 and the syringe pump 10 are connected, the injection port 8 and the one port of the flow path switching valve 14 forming the cleaning mechanism 13 are connected.

The needle 6 can be moved in a direction of a horizontal plane and a vertical direction by a needle driving portion (not shown). In a movable area of the needle 6, a rack disposing portion in which a sample rack 4 for retaining a plurality of vials 2 is disposed, the injection port 8, and a cleaning port 16 are positioned.

To carry out sampling of the sample, in a state in which the needle 6 and the syringe pump 10 are connected, the needle 6 moves to a position above the vial 2 for the sampling and then moves down to thereby enter the vial 2. When the syringe pump 10 is driven for suctioning, the sample in the vials 2 is taken in from a tip end of the needle 6. A sample loop 12 is provided on a flow path connected to the base end of the needle 6 and the taken-in sample is retained in the sample loop 12.

To inject the sampled sample into the analytical flow path of the liquid chromatograph, the needle 6 and the upstream analytical flow path 18 are connected, and the needle 6 is inserted into the injection port 8. As a result, the upstream analytical flow path 18, the sample loop 12, and the downstream analytical flow path 22 are connected in series to form the analytical flow path of the liquid chromatograph. A mobile phase is delivered from the upstream analytical flow path 18 by the solvent delivery pump 20 and the sample retained in the sample loop 12 is introduced into the downstream analytical flow path 22 together with the mobile phase. A separation column 24 and a detector (not shown) are provided in the downstream analytical flow path 22, the sample is separated into components in the analytical column 24, and the respective components are detected by the detector. Here, the needle 6, the needle driving portion (not shown), the syringe pump 10, and the sample loop 12 form a sampling mechanism for carrying out the sampling of the sample.

The cleaning mechanism 13 includes the flow path switching valve 14 and the cleaning port 16. It is possible to insert the needle 6 into the cleaning port 16 containing a cleaning solution to clean an inner face and an outer face of the needle 6. It is also possible to clean an inside of the flow path between the syringe pump 10 and the injection port 8 by inserting the needle 6 into the injection port 8, connecting the injection port 8 to a drain port provided to the flow path switching valve 14, taking the cleaning solution into the syringe pump 10, and discharging the cleaning solution from the tip end of the needle 6 into the injection port 8.

Figure 2A:
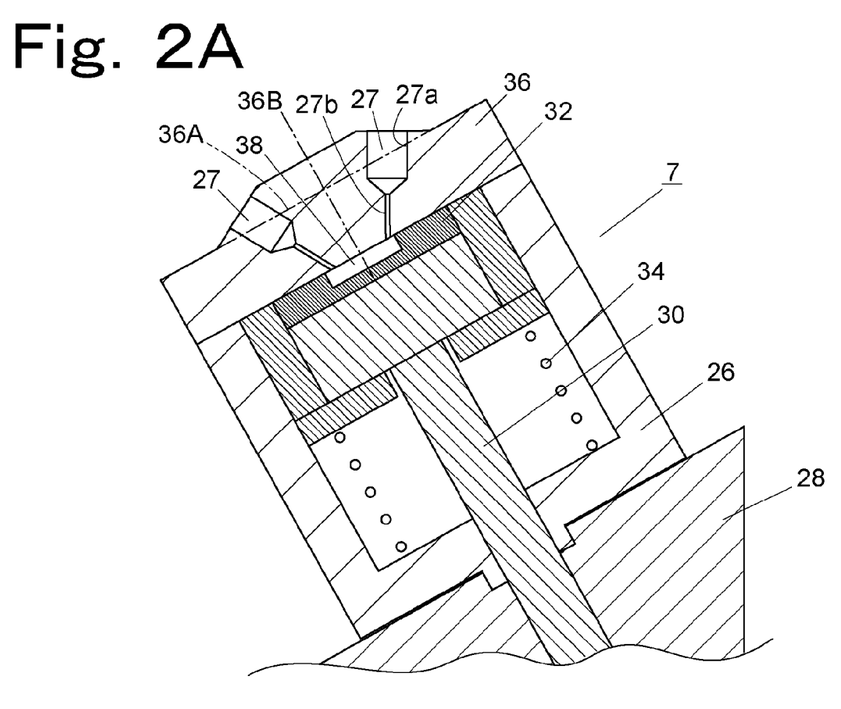
Figure 2B:
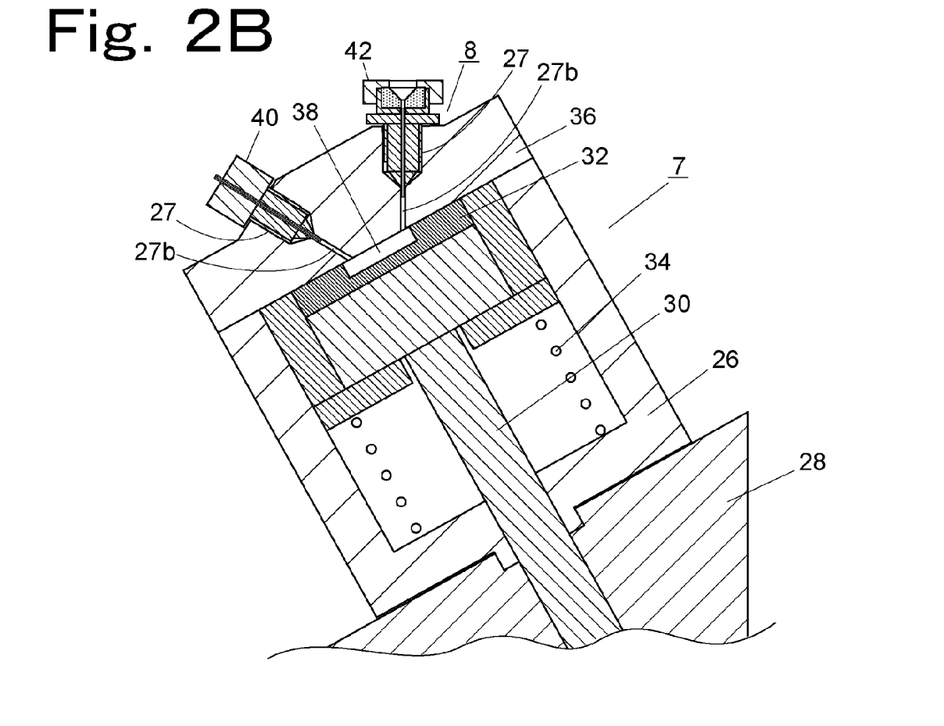

Next, a structure of the flow path switching valve 7 will be described with reference to FIG. 2.

All of the six pipe connecting ports 27 of the flow path switching valve 7 have the same structure and are disposed uniformly in the same plane 36A of the upper face of the stator 36. In this embodiment, each of the connecting holes 27 is inclined a certain angle with respect to an axis 36B passing through a center of the plane in which the connecting holes 27 are disposed.

The circular columnar rotor 32 is housed with its one circular face oriented toward an upper face side of a valve body 26 in the valve body 26. One end of a shaft 30 is connected to a center of the other circular face of the rotor 32, and the other end of the shaft 30 extends outside from a lower face of the valve body 26 and is driven for rotation by a driving mechanism (not shown).

The rotor 32 includes a port connecting flow path 38 for connecting adjacent ports of the stator 36. Bottom portions of the connecting holes 27 provided in the upper face of the stator 36 communicate with one end of the flow paths 27b. The respective flow paths 27b extend to a face facing the rotor 32 and are led to such positions as to be connected to the port connecting flow path 38 of the rotor 32. The stator 36 is retained by the valve body 26 and the rotor 32 is biased toward the stator 36 by a spring 34 so as to increase liquid tightness between the faces of the stator 36 and the rotor 32 facing each other.

On an inner peripheral face 27a of each of the connecting holes 27, a thread to be engaged by screwing with threads formed on an outer peripheral face of each of pipe connecting members 40 and the needle adaptor 42 is formed. The needle adaptor 42 is mounted into one of the connecting holes 27 by engagement of the threads by screwing to form the injection port 8. By mounting the needle adaptor 42 into the connecting hole 27, the needle 6 inserted into the needle adaptor 42 can be connected to the flow path 27b extending from the bottom portion of the connecting hole 27 to the face facing the rotor 32. The pipe connecting members 40 mounted to tip ends of pipes are fixed into the rest of the connecting holes 27 by engagement of the threads by screwing. By fixing the pipe connecting members 40 into the connecting holes 27, the pipes can be connected to the flow paths 27b extending from the bottom portions of the connecting holes 27 to the face facing the rotor 32.

In the flow path switching valve 7, by only rotating the shaft 30 a certain angle, a position of the port connecting flow path 38 of the rotor 32 is changed to change the adjacent ports to be connected by the port connecting flow path 38.

A disposing portion 28 of the flow path switching valve 7 is inclined a certain angle with respect to a horizontal direction so that a central axis of the connecting hole 27 in which the needle adaptor 42 is mounted is in a vertical orientation. A needle insertion portion of the needle adaptor 42 mounted into the connecting holes 27 is provided on the central axis. In this way, it is possible to insert the needle 6 into the needle insertion portion of the needle adaptor 42 by only driving the needle 6 to move it vertically downward from above the needle adaptor 42.

Figure 3A:
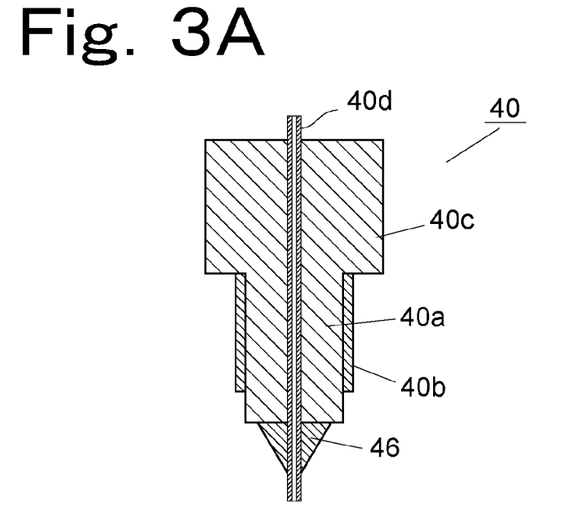

Examples of structures of the pipe connecting member 40 and the needle adaptor 42 will be described with reference to FIGS. 3A and 3B.

The pipe connecting member 40 has a circular columnar port fixing portion 40a. On an outer periphery of the port fixing portion 40a, a screwing portion 40b to be engaged by screwing with the thread formed on the inner peripheral face 27a of the connecting hole 27 is provided. One end of the port fixing portion 40a is locked to a tip end portion of a pipe 40d by a ferrule 46. The port fixing portion 40a locked by the ferrule 46 can rotate about the pipe 40d as an axis. A nut portion 40c is provided to the port fixing portion 40a on an opposite side from the ferrule 46. By rotating the nut portion 40c, the pipe connecting member 40 is fixed into the connecting hole 27 by engagement of the threads by screwing and the pipe 40d is connected to the flow path 27b.

The needle adaptor 42 includes a port fixing portion 42a having the same dimensions and shape as the port fixing portion 40a of the pipe connecting member 40, a screwing portion 42b provided on an outer periphery of the port fixing portion 42a, a needle seal housing 42c, a dummy pipe 42d, a needle seal fixing nut 42e, a needle seal 43, and a ferrule 48. The dummy pipe 42d has the same outer diameter as the pipe connected to the another connecting port 27 by the pipe connecting member 40.

The ferrule 48 is mounted to a tip end portion of the dummy pipe 42d. The port fixing portion 42a is locked by the ferrule 48 with the dummy pipe 42d inserted through the port fixing portion 42a. The needle seal housing 42c is provided to the port fixing portion 42a on an opposite side from the ferrule 48. The needle seal housing 42c has a recessed portion which is open upward and the needle seal 43 is housed in the recessed portion. The needle seal 43 is made of an elastic material such as a resin and a through hole for retaining the tip end of the needle 6, moving down from above, and serving as a flow path through which the solvent discharged from the tip end of the needle 6 flows is formed in a central portion of the needle seal 43. A through hole for connecting the through hole in the needle seal 43 and the dummy pipe 42d is formed in a bottom face of the recessed portion of the needle seal housing 42c.

To an upper portion of the needle seal housing 42c, the needle seal fixing nut 42e for fixing the needle seal is mounted. The needle seal fixing nut 42e has a recessed portion in one of its faces, and a thread is formed on an inner peripheral face of the recessed portion. A screwing portion 42f is formed on an outer periphery of the needle seal housing 42c and has a thread to be engaged by screwing with the thread formed on the inner peripheral face of the needle seal fixing nut 42e. The needle seal fixing nut 42e is mounted to an upper face side of the needle seal housing 42c. A central portion of the needle seal fixing nut 42e is open and forms a needle insertion portion 44, into which the needle is inserted, in cooperation with a recessed portion formed in a central portion of the needle seal 43.

By engaging and fixing the screwing portion 42b of the port fixing portion 42a of the needle adaptor 42 with and to the thread formed on the inner peripheral face 27a of the connecting hole 27 by screwing, the needle adaptor 42 can be mounted to the pipe connecting port. If the needle adaptor 42 is mounted to the pipe connecting port, the dummy pipe 42d is connected to the flow path 27b in the bottom portion of the connecting hole 27.

Figure 5:
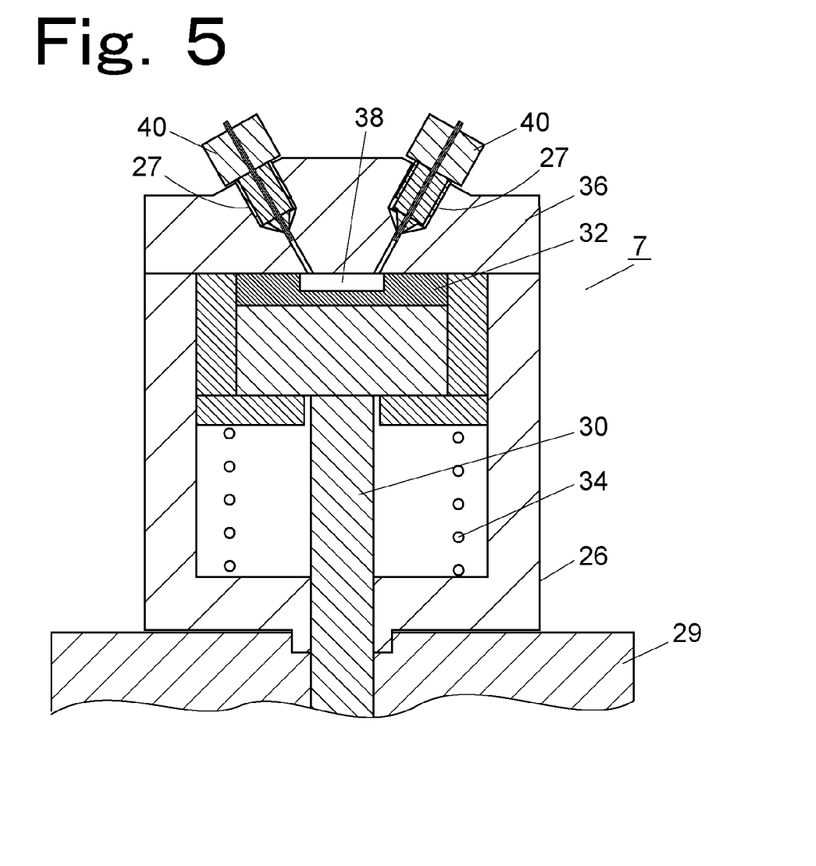
FIG. 5 is a sectional view showing a structure of a flow path switching valve used for a cleaning mechanism in the embodiment.

Because the port fixing portion 40a of the pipe connecting member 40 and the port fixing portion 42a of the needle adaptor 42 have the same shapes, the pipe connecting member 40 and the needle adaptor 42 can be fixed into the connecting holes 27 having the same structure. Therefore, it is unnecessary to provide the port for the injection port, having a special structure for mounting the needle adaptor 42, separately from the pipe connecting port. FIG. 5 shows a section of a flow path switching valve which does not require the injection port 8 and has the same structure as the flow path switching valve 7 except the shape of a disposing portion 29 is different. In this way, if the valves having the same structure can be used for the flow path switching valves for different uses, it is possible to reduce the number of parts and cost.

In other words, by disposing the flow path switching valve having the plurality of pipe connecting ports in such a way that the central axis of any one of the pipe connecting ports is in a vertical orientation and mounting the needle adaptor 42 to the pipe connecting port having the central axis in the vertical orientation in such a way that the central axis of the needle adaptor 42 is in the vertical orientation, it is possible to form the injection port 8 having the needle insertion portion 44 in the vertical upward orientation.

Figure 3B:
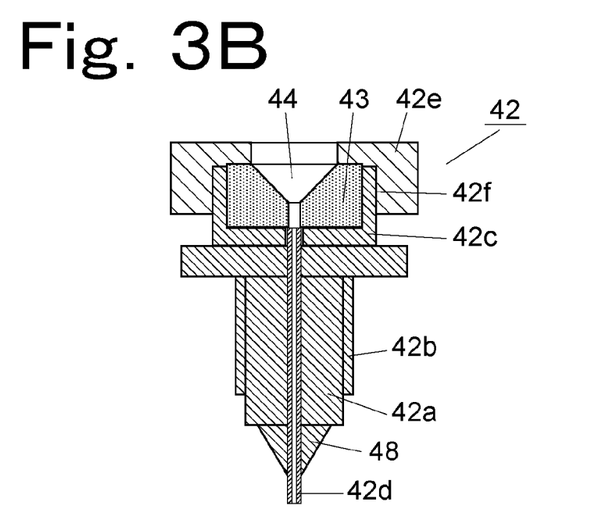
Figure 4:
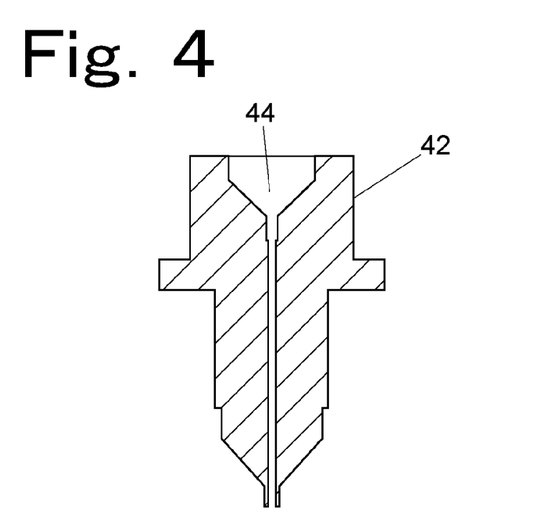
FIG. 4 is a sectional view showing another example of the needle adaptor.

The needle adaptor 42 may be formed by forming all of the port fixing portion 42a, the needle seal housing 42c, the dummy pipe 42d, the needle seal 43, and the ferrule 48 in FIG. 3B by, for example, integral molding by using an elastic material for forming the needle seal as shown in FIG. 4. In this case, the needle seal 43 need not be fixed, and therefore, a member corresponding to the needle seal fixing nut 42e is unnecessary.

Besides the example in FIG. 4, the needle adaptor 42 may, for example, have the port fixing portion 42a and the ferrule 48 integrally made of the same material, the port fixing portion 42a, the needle seal housing 42c, and the needle seal 43 integrally made of the same material, or the port fixing portion 42a, the needle seal housing 42c, and the dummy pipe 42d integrally made of the same material.

Although each of the ports of the flow path switching valve 7 is inclined the certain angle with respect to the axis passing through the center of the plane in which the ports are disposed in the above embodiment, the present invention is not limited to it and all the ports may be provided in vertical orientations. In this case, the flow path switching valve 7 is disposed horizontally and, by only mounting the needle adaptor 42 into any one of the connecting holes 27, it is possible to dispose the needle insertion portion 44 of the injection port 8 in a vertical upward orientation.

The invention claimed is:

1. A needle adaptor mounted to a flow path switching valve to form an injection port into which a needle is inserted to inject a sample from a tip end of the needle, comprising:
    a dummy pipe having the same outer diameter as a normal pipe connected to the flow path switching valve;
    a port fixing portion configured to be separated from the flow path switching valve for fixing and connecting the dummy pipe to one of a plurality of pipe connecting ports, wherein the flow path switching valve includes the plurality of pipe connecting ports, all of the pipe connecting ports having the same structure, and in which the needle adapter is mounted to one of the pipe connecting ports to form the injection port;
    a needle seal arranged on the end of the dummy pipe for retaining the tip end of the needle to connect the needle and the dummy pipe; and
    a needle seal housing mounted to the port fixing portion to retain the needle seal,
    wherein the port adapter is configured separately from the flow path switching valve, and
    wherein the port fixing portion and a port fixing, which is configured separately from the port fixing portion for the dummy pipe, of a pipe connecting member for connecting the normal pipe to the pipe connecting port have the same shape.

2. A needle adaptor according to claim 1, wherein the port fixing portion of the needle adaptor and the needle seal housing are integrally formed by using the same material.

3. A needle adaptor according to claim 2, wherein the dummy pipe, the port fixing portion of the needle adaptor, the needle seal, and the needle seal housing are integrally formed by using an elastic material for forming the needle seal.

4. An automatic sampler comprising:
    a syringe pump;
    a needle supported to move in horizontal and vertical directions for moving to a position of a sample vessel containing a sample, inserting its tip end portion into the sample vessel, and suctions the sample by suctioning operation of the syringe pump; and
    a flow path switching valve which includes a plurality of pipe connecting ports, all of the pipe connecting ports having the same structure, and in which the needle adaptor according to claim 1 is mounted to one of the pipe connecting ports to form an injection port.

5. An automatic sampler according to claim 4, wherein the respective pipe connecting ports of the flow path switching valve are disposed uniformly in a circumferential direction in the same plane to be inclined a certain angle with respect to the plane, and the flow path switching valve is disposed to be inclined such that the injection port is in a vertical orientation.

6. An automatic sampler according to claim 5, wherein the port fixing portion of the needle adaptor and the needle seal housing are integrally formed by using the same material.

7. An automatic sampler according to claim 6, wherein the dummy pipe, the port fixing portion of the needle adaptor, the needle seal, and the needle seal housing are integrally formed by using an elastic material for forming the needle seal.

8. An automatic sampler according to claim 4, further comprising a ferrule mounted to a tip end portion of the dummy pipe.

9. An automatic sampler according to claim 8, wherein the port fixing portion and the ferrule are integrally formed using the same material.

10. A needle adaptor according to claim 4, the port fixing portion having the dummy pipe within the port fixing portion and being provided with a screwing portion on an outer periphery of the port fixing portion.

11. A needle adaptor according to claim 1, further comprising a ferrule mounted to a tip end portion of the dummy pipe.

12. A needle adaptor according to claim 11, wherein the port fixing portion and the ferrule are integrally formed using the same material.

13. A needle adaptor according to claim 1, the port fixing portion having the dummy pipe within the port fixing portion and being provided with a screwing portion on an outer periphery of the port fixing portion.

* * * * *